United States Patent [19]

Tomlinson

[11] 4,322,466

[45] Mar. 30, 1982

[54] SHEET PRINTED WITH INVISIBLE INKS

[75] Inventor: Roderick P. J. Tomlinson, Glen Waverley, Australia

[73] Assignees: Lockley Services Pty. Ltd.; Graham Charles Barry; Norman John Field, all of Victoria, Australia; a part interest

[21] Appl. No.: 965,874

[22] Filed: Dec. 4, 1978

[30] Foreign Application Priority Data

Dec. 2, 1977 [AU] Australia ............................... PD2655
Dec. 2, 1977 [AU] Australia ............................... PD2656

[51] Int. Cl.³ ............................................... B41M 5/12
[52] U.S. Cl. ...................................... 428/199; 106/21; 282/27.5; 427/145; 427/288; 428/29; 428/537; 428/915; 428/916
[58] Field of Search ................... 106/21; 283/6; 427/7, 427/145, 261, 146, 288; 428/29, 199, 915, 916, 411, 537; 282/27.5

[56] References Cited

U.S. PATENT DOCUMENTS

| 2,355,884 | 8/1944 | McIntosh | 428/199 |
| 2,601,161 | 6/1952 | McIntosh | 428/199 X |
| 3,363,336 | 1/1968 | Skinner et al. | 35/9 G |
| 3,363,337 | 1/1968 | Skinner et al. | 35/9 G |
| 3,363,338 | 1/1968 | Skinner et al. | 35/9 G |
| 3,525,630 | 8/1970 | Phillips | 106/21 |

FOREIGN PATENT DOCUMENTS 133627 10/1919 United Kingdom .

OTHER PUBLICATIONS

*Daily Telegram–Guide to Gravure Printing*, London, 1968, pp. 2–13.

*Primary Examiner*—Bruce H. Hess
*Attorney, Agent, or Firm*—A. W. Breiner

[57] ABSTRACT

The invention relates to a developable surface comprising a carrier layer having thereon at least two deposits of one or more invisible inks in adjacent or overlapping relationship, said deposits in the developed state being unresolvable.

15 Claims, No Drawings

SHEET PRINTED WITH INVISIBLE INKS

This invention relates to a sheet of material having deposited thereon invisible inks, and to developers for treatment thereof.

The use of invisible inks has been widely known for well over 100 years. More particularly there have been many methods advocated for printing invisible inks on paper or like material which is capable of being rendered visible on contact with a colour reactant or developer. There has also been discovered a multitude of invisible inks and even the most basic type is still in use. One of the earliest types of invisible ink and process of use comprised impregnating the fibre of paper with a phenol-phthalein solution, this solution now being considered as part of the well known indicator system of invisible inks. When dried the solution became invisible on the surface to which it had been applied, however, by merely wetting the sheet with water, for example by dipping such therein, the colour was developed thereby producing the predetermined image printed on the paper.

To the skilled reader invisible inks can be selected from numerous wellknown alternatives, however, some of these are listed hereunder:

(1) a mixture of glycerine and lead acetate thickened with lead carbonate, which when developed gives black images;

(2) the indicator system mentioned before which typically comprises compounds such as thymol blue, cresol red, tri-nitro benzene, etc., each of these indicators when activated producing a characteristic colour;

(3) a mixture of cellulose nitrate and ethyl ether of a monoacetate of ethylene glycol; and (4) secondary amines of 3,3 bis (p-amino phenol) phthalide this compound being light sensitive and by absorption turns to a blue colour when activated thereby.

As mentioned above there are a host of alternatives for use as invisible inks known in the art, each of which display an individual colour when reacted with a suitable developer.

There has also been discovered and developed a variety of methods by which invisible inks can be applied to a supporting sheet to make them suitable for producing any desired effect. Such methods are again well known in the art and it is not thought necessary to elucidate further on these.

Whilst primarily invisible inks have been used in educational aids as a marking system, there has been little consideration of the use of these in the production of multi-colour images. The approaches to the later use have been all preoccupied with developing individual indicators each having a particular colour, e.g. purple. In this way, when, for example, a purple colour is necessary they choose the particular invisible ink which when reacted gives as close as possible to the desired colour and print such ink on the material. Whilst this approach has merit, it nevertheless relies heavily on correct mixing of the invisible ink and careful application thereof to the material. Further, with such complex mixtures it becomes increasingly difficult to obtain a single developer to develop a number of said inks simultaneously on a sheet. That is, a number of developers are necessary each developer corresponding to a particular colour or colours. It is not possible with such approach to easily obtain all intensities and shades of the colour spectrum as this would prove to be too difficult and expensive.

Further with the aforementioned educational aids, once used and the invisible ink activated such become useless.

It is therefore an object of this invention to simplify the necessary action to result in a developable surface having invisible ink deposited thereon which when activated is capable of giving a multi-coloured effect.

It is a further object to provide erasure compounds easily associated with conventional developers and invisible inks which cause the activated inks to once again take on that invisible form and thus capable of re-use.

With the first object in mind the problem has been approached from a different basis primarily revolving on the use of a finite number of invisible inks preferably those displaying the three primary colours, red, blue and yellow. Whilst the primary colors are selected this, of course, is not to preclude the use of colours other than the primary colours. The essential feature of this approach is that the invisible inks are printed in close proximity to each other and in sufficiently small amounts to be individually unresolvable in the developed state. Overlapping thereof can also be advantageous. Accordingly the overall appearance of the surface depending on the relative preponderance of certain color invisible inks is not the individual colours but the colour which would have been attained if they had actually been mixed prior to application. The resultant apparent colour can be easily varied to give colours spanning the full spectrum of colours by manipulating the respective amounts of each colour and their proximity to the other basic colours. Further by either spacing the individual deposits of colour(s) or varying the amounts thereof a difference in intensity of the overall colour is achieved. This is basically due to the greater exposure of the white paper to the viewer. By approaching the problem in this fashion it is possible to print one or more basic invisible inks onto the sheet in a predetermined pattern and by subsequent reaction with a developing compound or compounds to produce any type of multicoloured image very easily and economically.

Thus it will be appreciated that the present invention utilizes basic invisible inks deposited in small predetermined amounts which typically take the form of dots. As such, the invention is not to be interpreted as limited to the following discussion which recites the experimental compounds exhibiting the basic colours and sheets to which such are applied.

In developing the sheet capable of producing a multi-coloured effect, particular experimental evaluation was made on the utilization of chemical reactions which produce coloured species from colourless species with a change in hydrogen ion concentrations. From a broad range of available compounds which exhibit such change, three specific chemicals were selected whose coloured species is as close as possible to the desired primary colours. The use of primary colours is, of course, desirable in that by arranging respective amounts of such in unresolvable quantities the entire spectrum of apparent colour is obtained. The three compounds mentioned above were (1) para nitro phenol (PNP) which exhibits a change from colourless to yellow colour;

(2) 2 bis[(4 hydroxyphenyl) methyl] benzoic acid which exhibits a change from colourless to red colour; and (3) 3,3 bis[4 hydroxy 2 methyl 5 (1 methyl ethyl) phenol] 1 3H isobenzofuranone which exhibits a change from colourless to a blue colour.

In the course of experimentation it was found that the following were typical examples of usable compounds as well as those specified above:

Quinaldine red, quinoline blue, 2,4 dinitro phenol, 2,5 dinitro phenol, ethyl bis (2,4 dinitro phenol) acetate, cresolphthalein, nitramine and 1,3,5 trinitrobenzene.

As mentioned before, the closer the compound can be made to the primary colour then the more ultimate variations in apparent colour effect is possible in conjunction with other inks. In this respect particular care was taken to ensure the correct colour, colour density and image persistence. Where in fact industrial printing of the ink is being considered, these closely controlled conditions were necessary. Other considerations were the formulation and method of application of the subsequent developer and the type of paper used.

With regard to the paper used it was necessary that this have good printing characteristics, ability to resist continued application of aqueous alkali and a pH between 4 and 6. The reasons for this will become apparent in the following discussion of the ink. The ink used was formulated from a thickener, a polyol and a filler selected for its ability to be adjusted to a pH of 4 to 6 and thereby be suitable for dry off set printing. Typical inks based on shellac were unsuitable for these purposes. For example the active chemical as mentioned before, PNP, was incorporated into the ink using a co-solvent, e.g. an alcohol, glycol ether, aliphatic ester, pirolidone and or ketone. The developer used was formulated from an alkali so that when contacted with the printed ink, the hydrogen ion concentration of the ink decreased and the yellow colour evolved.

In another alternative the invisible ink may contain a colourless substance such as tannic or gallic acid whilst the developer contains a colourless metal ion such as Fe+++ or Cu++ in solution. In this system the developer produces the coloured image of the ink.

With respect to the second object of the invention there is provided a system of developing invisible inks and erasing the resultant developed inks comprising a surface having applied thereto one or more invisible inks, a developer applicable to said sheet to develop said ink(s) and an erasure compound application of which to the developed ink(s) causes same to re-assume an invisible state. In one embodiment the erasure compound and developer are in a combined form. Typically the erasure compound is a volatile alkali and is incorporated with the developer in suitable amounts to permit, a subsequent to colour activation of the ink by the developer, evaporation of the developer thereby allowing the hydrogen ion concentration of the ink to return to a level whereby it becomes colourless once again. For example para nitro phenol was considered, which ink is characterized by its ability to change colour from colourless to yellow colour. It was found that for PNP a solution of a conventional developer and volatile amines, in particular tetrahydro 2H 1,4 oxazine in a glycol/water vehicle, was capable of causing the ink to lose colour subsequent to the activation step. Typical of other combination developer-erasure species which were discovered are Ammonia, ethylamine, monoethanolamine, diethanolamine, and triethanolamine.

As an alternative to the above, instead of volatile alkalis it was found possible to use acid buffered vehicles in the inks. These gradually neutralize the alkali when applied from the developer. These acid buffers typically had a pH in the range of 3 to 5 and were fillers in the ink, the non-volatile alkalis in the developer having been buffered to a pH of 9 to 10.

As a further alternative it has been found possible to have an invisible ink containing a colourless dyestuff which can be oxidized initially by a developer containing an oxidant to give a colour and then returned to the invisible state by application of a reducing agent. Practically this alternative means the invisible ink can be printed onto a sheet and an oxidant-containing pen and a reducing agent-containing pen or spray can be provided for activation and de-activation of the ink. In the course of experimentation typical inks for use in this alternative contain aromatic amines such as p phenylene diamine and benzophenes. The developer containing the oxidant may be a solution containing hydrogen peroxide or benzoyl peroxides whereas the reducing agent which is the erasing chemical could be Sodium nitrite, cyclohexylamine nitrite, amyl nitrite, potassium nitrite and sodium sulphite.

The above specified chemicals are, of course, merely illustrative of the general type of chemical available for use in this alternative. They are certainly not to be interpreted as limiting on the usable options.

In another alternative the invisible ink may contain a colourless substance such as tannic or gallic acid whilst the developer contains a colourless metal ion such as Fe+++ or Cu++ in solution. In this system the developer produces the coloured image in the ink and subsequent treatment of the image with a chelating agent such as ethylene diamine tetra acetic acid, has the effect of rendering the image invisible. The sheet is therefore suitable for further development by again increasing the concentration of the metal ion with the developer. Other suitable complexing substances are Tetramines, glyoximes and benzophenones.

The following are examples of working formulations of invisible inks in the present invention. More particularly formulations of the primary colours may be as follows:

|  | % by weight |
|---|---|
| Red | |
| 2 [bis (4 hydroxyphenyl) methyl] benzoic acid | 10.0 |
| 2 (2-Ethoxyethoxy) ethanol | 20.0 |
| 9 Octadecene-1-ol | 67.0 |
| filicic acid | 3.0 |
| | 100.0 |
| Blue | |
| 3,3 bis [4 hydroxy 2 methyl 5 (1 methylethyl) phenyl] 1 3H isobenzofuranone | 3.0 |
| 2 (2-Ethoxyethoxy) ethanol | 20.0 |
| 9 Octadecene-1-ol | 74.0 |
| filicic acid | 3.0 |
| | 100.0 |
| Yellow | |
| 4 nitro phenol | 15.0 |
| 2 (2 Ethoxyethoxy) ethanol | 20.0 |
| 9 Octadecene-1-ol | 62.0 |
| filicic acid | 3.0 |
| | 100.0 |

The following are examples of the developer and erasure compounds:

| Developer | % by weight |
|---|---|
| Potassium carbonate | 10.0 |
| Potassium hydroxide | 5.0 |
| Water | 85.0 |
|  | 100.0 |
| Eraser |  |
| Citric acid | 20.0 |
| Water | 80.0 |
|  | 100.0 |
| Self erasing Developer |  |
| Potassium Carbonate | 2.0 |
| .880 Ammonia | 10.0 |
| Water | 88.0 |
|  | 100.0 |

I claim:

1. A developable surface comprising a carrier layer capable of accepting print and having printed thereon in a predetermined pattern a plurality of individual deposits of at least two different invisible inks in adjacent and intermingling relationship, said individual deposits in the developed state not being optically resolvable as different colors, and with said plurality of deposits being optically resolvable as a blended color of the said different inks.

2. A developable surface according to claim 1 wherein said invisible inks are selected from a group thereof which in the developed state displays primary colours.

3. A developable surface according to claim 1 wherein the invisible inks are selected from a group of 2 [bis(4 hydroxyphenyl) methyl] benzoic acid, 3,3 bis[4 hydroxy 2 methyl 5 (1 methylethyl) phenyl] 1 3H isobenzofuranone and 4 nitro phenol.

4. A developable surface according to claim 3 wherein said group also includes para nitro phenol, quinoline blue, quinaldine red, 2,4 dinitro phenol, 2,5 dinitro phenol, ethyl bis(2,4 dinitro phenol) acetate, cresolphthalein, nitramine and 1,3,5 trinitrobenzene.

5. A developable surface according to claim 1 wherein said carrier layer is a paper product resistant to attack from aqueous alkali and having a pH between 4 and 6.

6. A developable surface according to claim 1 wherein said invisible ink also includes a solvent.

7. A developable surface according to claim 6 wherein said solvent is an alcohol or glycol ether, aliphatic ester, pirolidone or ketone.

8. A developable surface according to claim 1 wherein said invisible ink also includes a colorless substance selected from the group including tannic or gallic acid.

9. A developable surface according to claim 1 wherein all the invisible inks are developable by a single developer compound.

10. A developable surface according to claim 9 wherein said developer is an alkali.

11. A developable surface according to claim 9 wherein said developer contains a colorless metal ion.

12. A developable surface according to claim 11 wherein said metal ion is $Fe^{+++}$ or $Cu^{++}$.

13. A developable surface according to claim 1 wherein all the invisible inks are developable with a plurality of developer compounds.

14. A developable surface according to claim 13 wherein said developer is an alkali.

15. A developable surface according to claim 13 wherein said developer contains a colorless metal ion.

* * * * *